United States Patent
Zhou et al.

(10) Patent No.: US 8,481,754 B2
(45) Date of Patent: Jul. 9, 2013

(54) QUINOID SILAFLUORENE ORGANIC SEMICONDUCTOR MATERIAL, PREPARATION METHOD AND USE THEREOF

(75) Inventors: Mingjie Zhou, Shenzhen (CN); Jie Huang, Shenzhen (CN); Hui Liu, Shenzhen (CN)

(73) Assignee: Ocean's King Lighting Science & Technology Co., Ltd., Shenzhen (CN)

( * ) Notice: Subject to any disclaimer, the term of this patent is extended or adjusted under 35 U.S.C. 154(b) by 0 days.

(21) Appl. No.: 13/699,948

(22) PCT Filed: May 24, 2010

(86) PCT No.: PCT/CN2010/073115
§ 371 (c)(1),
(2), (4) Date: Nov. 26, 2012

(87) PCT Pub. No.: WO2011/147071
PCT Pub. Date: Dec. 1, 2011

(65) Prior Publication Data
US 2013/0072693 A1    Mar. 21, 2013

(51) Int. Cl.
*C07D 333/04* (2006.01)
*C07F 7/10* (2006.01)

(52) U.S. Cl.
USPC .............................................. 549/4; 556/406

(58) Field of Classification Search
USPC ............................................... 556/406; 549/4
See application file for complete search history.

(56) References Cited

FOREIGN PATENT DOCUMENTS

| | | |
|---|---|---|
| CN | 101298459 | 11/2008 |
| JP | 2003-206289 | 7/2003 |

OTHER PUBLICATIONS

International Search Report of PCT/CN2010/073115 dated Feb. 10, 2011, 6 pages total.

*Primary Examiner* — Kristin Vajda
(74) *Attorney, Agent, or Firm* — Hamre, Schumann, Mueller & Larson, P.C.

(57) ABSTRACT

A quinoid silafluorene organic semiconductor material represented by formula (I) is disclosed, in which $R_1$, $R_2$, $R_5$ and $R_6$ are selected from H or $C_1$-$C_{20}$ alkyl; $R_3$ and $R_4$ are selected from $C_1$-$C_{20}$ alkyl; m and n are an integer of 0 to 10. A preparation method of said quinoid silafluorene organic semiconductor material and the use thereof are also disclosed.

9 Claims, 2 Drawing Sheets

QUINOID SILAFLUORENE ORGANIC SEMICONDUCTOR MATERIAL, PREPARATION METHOD AND USE THEREOF

TECHNICAL FIELD

The present invention relates to the technical field of synthesis of organic compound, particularly, to a quinoid silafluorene organic semiconductor material, preparation method and use thereof.

BACKGROUND

The economy all over the world today is built on the basis of fossil fuel, such as coal, oil and natural gas. However, all of these non-reproducible fossil energies are continuously exhausted. Since the beginning of the 21st century, the global energy problems and the consequent problems of environmental pollution and climate warming are becoming more and more prominent and gradually intensified. Because of the outstanding advantages of wide and broad distribution, large scale resources, pollution-free, clean, safe, and easy to obtain, the solar energy is considered to be one of the most promising renewable energy. The solar cell converts the solar energy to electric energy directly, thus it is a practicable method for utilizing the solar energy. However, currently commercial solar cells are all limited to the silicon-based inorganic solar cell, but the cost is so high that people cannot accept it, thus the scope of their use is significantly limited. For a long time, to reduce the cost of the solar cell and expand the range of application, people have been looking for new type of solar cell materials.

The organic solar cell is a new type of solar cell. Compared to the disadvantages of limited source, expensive price, toxic, complicated manufacturing process and high cost of the inorganic semiconductor material, the organic solar cell has the incomparable advantages that the inorganic solar cell doesn't have, such as wide sources of raw materials, a variety of structures and good adjustability, low cost, safety and environmental protection, simple manufacturing process, light weight, possibly to produce in a large flexibly area, and the like, it can be widely used in construction, lighting and power generation and other areas, thus it has an important development and application prospects. Therefore, many domestic and foreign research institutes and enterprises are paying considerable attention and investment to the field of organic solar cell. However, until now, the photoelectric conversion efficiency of the organic solar cell is much lower than that of inorganic solar cell. Therefore, the development of new organic photovoltaic materials has much importance for improving the efficiency of organic solar cells and other semiconductor devices.

SUMMARY

To overcome the above shortcomes in prior art, the present invention provides a quinoid silafluorene organic semiconductor material with high solubility and stability, and low energy band gap, so as to broaden the absorption range of solar spectrum of the solar cell, improve the photoelectric conversion efficiency thereof.

Another object of the present invention is to provide a method for manufacturing the quinoid silafluorene organic semiconductor material with simple process, high yield, and it is easy to operate and control.

A further object of the present invention is to provide the use of the aforementioned quinoid silafluorene organic semiconductor material in the fields of organic photoelectric materials, polymer solar cells, organic electroluminescent elements, organic field effect transistors, organic optical storage elements, organic nonlinear materials and/or organic laser elements.

The above-mentioned technical problems can be solved through the following technical solutions:

A quinoid silafluorene organic semiconductor material, the general formula (I) thereof is as follows:

(I)

wherein, $R_1$, $R_2$, $R_5$ and $R_6$ are independently selected from the group consisting of H and $C_1$-$C_{20}$ alkyl, $R_3$ and $R_4$ are independently $C_1$-$C_{20}$ alkyl, m and n are independently integers of 0-10.

And, a method for manufacturing a quinoid silafluorene organic semiconductor material, comprising:

compounds A, B, C and D with following general formulae are provided separately:

A:

B:

C:

D:

wherein $R_1$, $R_2$, $R_5$ and $R_6$ are independently selected from the group consisting of H and $C_1$-$C_{20}$ alkyl, $R_3$ and $R_4$ are independently $C_1$-$C_{20}$ alkyl, m and n are independently integers of 0-10;

in an alkaline environment and with the presence of a catalyst and an organic solvent, the Suzuki coupling reaction of compounds A, B and C is carried out to give the compound E of following formula:

(E)

with the presence of an organic solvent, the bromination reaction of compound E and N-bromo-succinimide is carried out to give a dibromo compound of compound E;

with the presence of a catalyst, a condensing agent and an organic solvent, the condensation reaction of the dibromo compound of compound E and malononitrile is carried out to give the quinoid silafluorene organic semiconductor material of general formula (I), wherein, m and n are independently integers of 1-10;

alternatively, with the presence of a catalyst, a condensing agent and an organic solvent, the condensation reaction of compound D and malononitrile is carried out to give the quinoid silafluorene organic semiconductor material of general formula (I), wherein m=n=0, Furthermore, the use of the quinoid silafluorene organic semiconductor material of the present invention in the fields of organic photoelectric materials, polymer solar cells, organic electroluminescent elements, organic field effect transistors, organic optical storage elements, organic nonlinear materials and/or organic laser elements.

The quinoid silafluorene organic semiconductor material and the preparation method thereof according to the present invention have at least following advantages compared to the prior art:

1. it is easy to introduce an alkyl into the quinoid silafluorene organic semiconductor material, which increases the solubility of the material;
2. the dicyanovinyl ($=C(CN)_2$) contained therein is a strong electron withdrawing group, when introduced into a quinoid structure with strong conjugacy, it not only increases the stability of the material, but also facilitates lowering the energy band gap of the material, thus the absorption range of solar spectrum is broadened, and the photoelectric conversion efficiency is improved;
3. the method for manufacturing the quinoid silafluorene organic semiconductor material is simply, has the advantages of high yield, mild condition for reaction, easy to operate and control, and it is suitable for industrial production.

DETAILED DESCRIPTION OF THE PREFERRED EMBODIMENTS

Objects, advantages and embodiments of the present invention will be explained below in detail with reference to the accompanying drawings and embodiments. However, it should be appreciated that the following description of the embodiment is merely exemplary in nature and is not intended to limit this invention.

Figure 1:
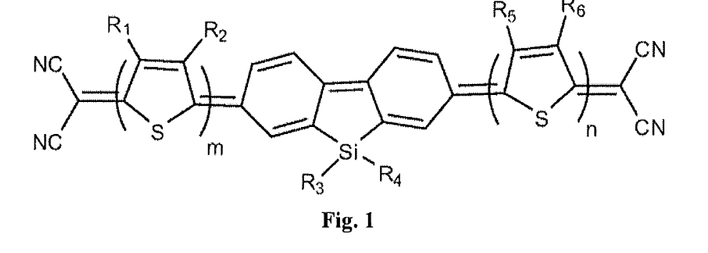
FIG. 1 is the general formula of the quinoid silafluorene organic semiconductor material according to the embodiments of the present invention.

Referring to FIG. 1, a quinoid silafluorene organic semiconductor material according to the embodiments of the present invention is shown, the general formula (I) thereof is as follows:

(I)

(I)

wherein, $R_1$, $R_2$, $R_5$ and $R_6$ are independently selected from the group consisting of —H and $C_1$-$C_{20}$ alkyl, $R_3$ and $R_4$ are independently $C_1$-$C_{20}$ alkyl, m and n are independently integers of 0-10. $R_1$, $R_2$, $R_5$ and $R_6$ are preferably —$C_6H_{13}$ or —$C_{20}H_{41}$ alkyl, $R_3$ and $R_4$ are preferably —$CH_3$, —$C_6H_{13}$ or —$C_{20}H_{41}$ alkyl.

In the above quinoid silafluorene organic semiconductor material according to the embodiments of the present invention, it is easy to introduce an alkyl, and the introduction of alkyl improves the original rigidity of the molecular, thereby in the same solvent, compared to the molecular without introduction of alkyl, the solubility of the quinoid silafluorene organic semiconductor material according to the embodiments of the present invention, is increased effectively, meanwhile the quinoid silafluorene organic semiconductor material contains dicyanovinyl ($=C(CN)_2$), which is a strong electron withdrawing group, when introduced into a quinoid structure with strong conjugacy, it not only increases the stability of the material, but also facilitates lowering the energy band gap of the material, thus the absorption range of solar spectrum is broadened, and the photoelectric conversion efficiency is improved. And the fluorenyl increases the density of backbone electron atmosphere of the semiconductor material effectively, narrows the band gap of the semiconductor material, and increases the potential application value thereof in the organic semiconductor material.

Also, the embodiments of the present invention provide the method for manufacturing the quinoid silafluorene organic semiconductor material, comprising:

(1) compounds A, B, C and D with following general formulae are provided separately:

A:

B:

C:

D:

wherein $R_1$, $R_2$, $R_5$ and $R_6$ are independently selected from the group consisting of H and $C_1$-$C_{20}$ alkyl, $R_3$ and $R_4$ are independently $C_1$-$C_{20}$ alkyl, m and n are independently integers of 0-10;

(2) in an alkaline environment and with the presence of a catalyst and an organic solvent, the Suzuki coupling reaction of compounds A, B and C is carried out to give the compound E, the chemical equation thereof is as follows:

(3) with the presence of an organic solvent, the bromination reaction of compound E and N-bromo-succinimide is carried out to give a dibromo compound F of compound E, the chemical equation thereof is as follows:

(4) with the presence of a catalyst, a condensing agent and an organic solvent, the condensation reaction of the dibromo compound F of compound E and malononitrile is carried out to give the quinoid silafluorene organic semiconductor material of following general formula (I), wherein, m and n are independently integers of 1-10, the chemical equation thereof is as follows:

Alternatively, with the presence of a catalyst, a condensing agent and an organic solvent, the condensation reaction of compound D and malononitrile is carried out to give the quinoid silafluorene organic semiconductor material of general formula (I'), the chemical equation thereof is as follows:

wherein general formula (I') is a special case of general formula (I) when both m and n are 0.

The compounds B and C in the above step (1) are commercially available, or may be prepared by the exiting synthesis method, and the method for preparing compound A comprises following steps:

a) with the presence of an organic solvent, the reaction of 4,4'-dibromo-2,2'-diiodo-biphenyl, alkyl lithium derivative and dialkyl dichlorosilane is carried out to give a compound of 2,7-dibromo-9,9-dialkylsilafluorene, the chemical equation of this step is as follows:

b) with the presence of an organic solvent, the reaction of 2,7-dibromo-9,9-dialkyl silafluorene compound, alkyl lithium derivative, 2-isopropoxy-4,4,5,5-tetramethyl-1,3,2-dioxaborolane is carried out to give the compound A, the chemical equation of this step is as follows:

In the above step a), the molar ratio of 4,4'-dibromo-2,2'-diiodo-biphenyl, alkyl lithium derivative, dialkyl dichlorosilane is preferably 1.0:2.0-4.0:2.0-4.0; the said organic solvent is preferably one or more selected from the group consisting of tetrahydrofuran, diethyl ether, dichloromethane, chloroform, ethyl acetate; the temperature of this step is preferably −100 to −25° C., the duration thereof is preferably 24-48 hours.

In the above step b), the molar ratio of 2,7-dibromo-9,9-dialkyl silafluorene compound, alkyl lithium derivative, 2-isopropoxy-4,4,5,5-tetramethyl-1,3,2-dioxaborolane is preferably 1.0:2.0-4.0:2.0-4.0; the said organic solvent is preferably one or more selected from the group consisting of tetrahydrofuran, diethyl ether, dichloromethane, chloroform, ethyl acetate; the temperature of this step is preferably −100 to −25° C., the duration thereof is preferably 24-48 hours.

The above steps a) and/or b) may be carried out under oxygen or oxygen-free environment. The oxygen-free environment is preferred, and the oxygen-free environment may be achieved by vacuum evacuation or being filled with in inert gas, and be filled with inert gas is preferred, the inert gas is commonly used in prior art, e.g. nitrogen, argon, the nitrogen is preferred. This is because the reaction under oxygen-free environment may have an increased yield in every reaction step, as oxygen is a very active ingredient, which may react with the reactants, interfering with the progress of the reaction, thus reducing the product yield. The alkyl lithium derivative in steps a) and/or b) is preferably one or more selected from the group consisting of N-butyl lithium, tert-butyl lithium, methyl lithium and phenyl lithium.

In the general formula of compound E obtained by the Suzuki coupling reaction in the above step (2), when m=n=0, in step (1) only compounds D and malononitrile take part in the condensation reaction, and the quinoid silafluorene organic semiconductor material of general formula (I) with m=n=0 is obtained, wherein the compound D is commercially available; when m=0 and 0<n≦10, only compounds A and C are selected for the coupling reaction of step (2) to obtain the quinoid silafluorene organic semiconductor material of general formula (I) with m=0 and 0<n≦10; when n=0, 0<m≦10, only compounds A and B are selected for the coupling reaction of step (2) to obtain the quinoid silafluorene organic semiconductor material of general formula (I) with n=0 and 0<m≦10; when 0<m≦10 and 0<n≦10, compounds A, B and C all are selected for the coupling reaction of step (2) to obtain the quinoid silafluorene organic semiconductor material of general formula (I) with 0<m≦10 and 0<n≦10, when 0<m≦10 and 0<n≦10, the molar ratio of compounds A, B and C is preferably 1.0:1.0-1.5:1.0-1.5, wherein, the molar ratio of compound B and C is preferably 1:1.

The alkali in the alkaline environment of the Suzuki coupling reaction step of the step (2) is one or more selected from the group consisting of NaOH, $Na_2CO_3$, $NaHCO_3$ and tetraethyl ammonium hydroxide; the said catalyst is preferably one or more selected from the group consisting of $Pd(PPh_3)_4$, $Pd_2(dba)_3$/$P(o\text{-}Tol)_3$, $Pd(PPh_3)_2Cl_2$, and the amount thereof is 0.05%-20% molar percent of that of the compound A; the said organic solvent is preferably one or more selected from the group consisting of ethylene glycol dimethyl ether, tetrahydrofuran, diethyl ether, dichloromethane, chloroform and ethyl acetate. The temperature of the Suzuki coupling reaction is preferably 75-120° C., the duration thereof is preferably 12-72 hours. A catalyst is necessary for the Suzuki coupling reaction, since the catalyst has the following features: first, it can effectively improve the yield of Compound E of the present invention; second, it can improve the reaction rate of the Suzuki coupling reaction, and shorten the reaction time, increase production efficiency; third, as the catalyst is necessary for the Suzuki coupling reaction, which may react with one reactant in the reaction to obtain an intermediate product, thereby the Suzuki coupling reaction can be carried out.

The above Suzuki coupling reaction can be carried out in an oxygen or oxygen-free environment. Preferably it is carried out in an oxygen-free environment, and the oxygen-free environment can be achieved by vacuum evacuation or being filled with an inert gas, preferably by being filled with an inert gas, the inert gas is commonly used in the art, such as nitrogen, argon, etc., and nitrogen is preferred. This is because in an oxygen-free environment, the yield of the compound E may be improved, as oxygen is a very active ingredient, which can react with the reactants, interfering with the progress of the reaction, thus reducing the product yield.

The molar ratio of compound E and N-bromo-succinimide in the above bromination reaction step of step (3) is preferably 1.0:2.0-2.5; the organic solvent is preferably one or more selected from the group consisting of N,N-dimethyl formamide (DMF), tetrahydrofuran, diethyl ether, dichloromethane, chloroform, ethyl acetate and acetic acid. The temperature of the bromination reaction is preferably −5-30° C., the duration thereof is preferably 12-48 hours.

The molar ratio of the dibromo compound of compound E and malononitrile in the above condensation reaction of the step (4) is preferably 1.0:2.0-10; the organic solvent is preferably one or more selected from the group consisting of ethylene glycol dimethyl ether, tetrahydrofuran, diethyl ether, dichloromethane, chloroform and ethyl acetate. The said condensing agent is preferably one or more selected from the group consisting of NaH and sodium alkoxide, and more preferably the condensing agent is NaH, wherein the sodium alkoxide is preferably but not limited to sodium methoxide, sodium tert-butoxide. The temperature of the condensation reaction is preferably 75-120° C., the duration thereof is preferably 12-72 hours; the said catalyst is preferably one or more selected from the group consisting of $Pd(PPh_3)_4$, $Pd_2(dba)_3$, $Pd(PPh_3)_2Cl_2$, the amount thereof is 0.05%-20% molar percentage of that of the dibromo compound of compound E.

In this method for manufacturing a quinoid silafluorene organic semiconductor material, the reactants may be added in a certain ratio, and no other special equipment and environmental are required, the method has a simple process, high yield, mild reaction condition, it is easy to operate and control, suitable for industrial production.

Because of the above advantages of the quinoid silafluorene organic semiconductor material, the quinoid silafluorene organic semiconductor material may be used in the fields of organic photoelectric materials, polymer solar cells, organic electroluminescent elements, organic field effect transistors, organic optical storage elements, organic nonlinear materials and/or organic laser elements.

The present invention will be explained in detail referring to Examples.

Example 1

Preparation of the Quinoid Silafluorene Organic Semiconductor Material with Following Structural Formula $I_1$ 1) Preparation of 2,7-dibromo-9,9-dimethyl silafluorene, the structural formula and preparation method thereof are as follows:

under the protection of nitrogen, 5.64 g of 4,4'-dibromo-2,2'-diiodo biphenyl was dissolved in 40 mL of THF, cooled to −25° C., to the solution was added dropwise 20.00 mL of n-butyl lithium solution (n-butyl lithium/n-hexane in 1.0 mol/L). After 2 hours of reaction, 1.29 g of dimethyl dichlorosilane was added, and the reaction was continued for another 24 hours. After the completion of the reaction, a deionized water was added and the resulting mixture was extracted with diethyl ether, then dried over anhydrous magnesium sulfate, rotary evaporated, and column chromatographed to give the product. MALDI-TOF-MS (m/z): 368.1 ($M^+$);

2) Preparation of the quinoid silafluorene organic semiconductor material with following structural formula $I_1$, the method for preparation is as follows:

in ice bath, 3.14 g of malononitrile was added to the suspension of 2.45 g of sodium hydride (60% in oil solution) in 50 mL of ethylene glycol dimethyl ether, then the mixture was warmed to room temperature, stirred for 20 minutes and 3.68 g of 2,7-dibromo-9,9-dimethyl silafluorene and 0.54 g of $PdCl_2(PPh_3)_2$ were added. The mixture was heated to 120° C. for 12 hours, cooled to 0° C., and saturated $Br_2/H_2O$ solution was added. A water was added, and the resulting mixture was vacuum filtered, washed with water, dried, and column chromatographed to give the product. MALDI-TOF-MS (m/z): 336.4 ($M^+$).

Example 2

Preparation of the Quinoid Silafluorene Organic Semiconductor Material with Following Structural Formula I₂

(I₂)

1) Preparation of 2,7-dibromo-9,9-dihexyl silafluorene, the structural formula and preparation method are as follows:

Under the protection of argon, 6.00 g of 4,4'-dibromo-2,2'-diiodo biphenyl was dissolved in 100 mL of THF, cooled to −100° C., then to the solution 42.55 mL of methyl lithium solution (methyl lithium/n-hexane in 1.0 M) was added dropwise. After 12 hours of reaction, 5.70 g dihexyl dichlorosilane was added, and the reaction was continued for another 48 hours, the reaction was completed, then a water was added, and the mixture was extracted with diethyl ether, dried over anhydrous magnesium sulfate, rotary evaporated, and column chromatographed to give the product, MALDI-TOF-MS (m/z): 508.4 (M⁺);

2) Preparation of 2,7-bis(4,4,5,5-tetramethyl-1,3,2-dioxaborolan)-9,9-dihexyl silafluorene, the structural formula and preparation process thereof are as follows:

At −25° C., under nitrogen, 10.00 mL (2.00 M) of n-butyl lithium solution was added to a reaction flask containing 5.08 g of 2,7-dibromo-9,9-dihexyl silafluorene and 50 mL of tetrahydrofuran, stirred for 2 hours, then 4.17 mL of 2-isopropoxy-4,4,5,5-tetramethyl-1,3,2-dioxaborolane was added dropwise slowly, and stirred for another 24 hours, the reaction was completed, then the fluid mixture was poured into water and the solution was extracted with diethyl ether, dried over anhydrous magnesium sulfate, rotary evaporated, and column chromatographed to give a solid product, MALDI-TOF-MS (m/z): 602.5 (M⁺);

3) Preparation of 3,7-bis(thiophen-2-yl)-9,9-dihexyl silafluorene, the structural formula and preparation process thereof are as follows:

Under the protection of nitrogen, to a reaction flask containing 3.01 g of 2,7-bis(4,4,5,5-tetramethyl-1,3,2-dioxaborolan)-9,9-dihexyl silafluorene, 1.63 g of 2-bromothiophene and 0.34 g of Pd(PPh₃)₄, 40 mL of aqueous NaHCO₃ solution (1 M) and ethylene glycol dimethyl ether (60 mL) were added, after purged with nitrogen for 1 hour, the solution was heated at 120° C. for 12 hours, the reaction was completed, then the mixture was filtered and dried in vacuo, column chromatographed to give a solid product, MALDI-TOF-MS (m/z): 514.9 (M⁺);

4) Preparation of 3,7-bis(5-bromo-thiophen-2-yl)-9,9-dihexyl silafluorene, the structural formula and preparation process thereof are as follows:

At −5° C., 0.71 g of NBS was added in batch to a reaction flask containing 1.30 g of 5,5-dihexyl-3,7-bis(thiophen-2-yl)-4H-bis(silafluorene) and 20 mL of DMF, stirred for 48 hours. After the completion of the reaction, the fluid mixture was poured into ice-water for quenching, then it was extracted with chloroform, dried over anhydrous magnesium sulfate, and rotary evaporated, and column chromatographed to give the product, MALDI-TOF-MS (m/z): 672.7 (M⁺);

Preparation of the quinoid silafluorene organic semiconductor material of structural formula I₂, the method for preparation is as follows:

In ice bath, 1.57 g of malononitrile was added to the suspension of 0.19 g of sodium hydride (sodium hydride in oil in 60 wt %) in 25 mL of ethylene glycol dimethyl ether, then warmed to room temperature, stirred for 30 minutes and 0.67 g of 5,5-di-hexyl-3,7-bis(5-bromo-thiophen-2-yl)-4H-bis(silafluorene) and 0.034 g of PdCl₂(PPh₃)₂ were added. The mixture was heated at 75° C. for 72 hours, then cooled to 0° C., and saturated Br₂/H₂O solution was added. A water was added, and the mixture was vacuum filtered, washed with water, dried, and column chromatographed to give the product. MALDI-TOF-MS (m/z): 640.9 (M⁺).

Example 3

Preparation of the Quinoid Silafluorene Organic Semiconductor Material of Following Structural Formula I₃

(I₃)

1) preparation of 2,7-bis(4,4,5,5-tetramethyl-1,3,2-dioxaborolan)-9,9-dihexyl silafluorene, the detailed preparation process thereof is the same as step 2) of Example 2, and its structural formula is as follows:

2) preparation of 3,7-bis(4-hexyl thiophen-2-yl)-9,9-dihexyl silafluorene, and the structural formula and preparation process are as follows:

Under the protection of nitrogen, to a reaction flask containing 3.01 g of 2,7-bis(4,4,5,5-tetramethyl-1,3,2-dioxaborolan)-9,9-dihexyl silafluorene, 2.68 g of 2-bromo-4-hexyl thiophene and 0.15 g of Pd(PPh₃)₄, 30 mL of aqueous NaOH (1 M) solution and chloroform (50 mL) were added, purged with nitrogen for 1 hour, then heated at 75° C. for 72 hours, the reaction was completed, the mixture was filtered and dried in vacuo, column chromatographed to give a solid product, MALDI-TOF-MS (m/z): 683.2 (M⁺);

3) preparation of 3,7-bis(5-bromo-4-hexyl thiophen-2-yl)-9,9-dihexyl silafluorene, and the structural formula and preparation process thereof are as follows:

At 0° C., 0.89 g of NBS was added in batch to a reaction flask containing 1.37 g of 5,5-di-hexyl-3,7-bis(4-hexyl thiophen-2-yl)-4H-bis(silafluorene) and 40 mL of DMF, stirred for 12 hours. After the completion of the reaction, the fluid mixture was poured into ice-water for quenching, then the solution was extracted with chloroform, dried over anhydrous magnesium sulfate, rotary evaporated, and column chromatographed to give the product, MALDI-TOF-MS (m/z): 841.0 (M⁺);

4) preparation of the quinoid silafluorene organic semiconductor material of structural formula I₃, its preparation process is as follows:

in ice bath, 0.25 g of malononitrile was added to the suspension of 0.21 g of sodium hydride (sodium hydride in an oil solution in 60 wt %) in 30 mL of ethylene glycol dimethyl ether, warmed to room temperature and stirred for 30 minutes, then to the solution was added 0.84 g of 5,5-di-hexyl-3,7-bis(5-bromo-4-hexyl thiophen-2-yl)-4H-bis(silafluorene) and 0.038 g of PdCl₂(PPh₃)₂, and heated at 90° C. for 52 hours, then cooled to 0° C., saturated Br₂/H₂O solution was added, a water was added, then the mixture was vacuum filtered, and washed with water, dried, and column chromatographed to give the product, MALDI-TOF-MS (m/z): 809.3 (M⁺).

Example 4

Preparation of the Quinoid Silafluorene Organic Semiconductor Material of Following Structural Formula I₄

(I₄)

1) Preparation of 2,7-dibromo-9,9-bis-eicosyl silafluorene, and its structural formula and preparation method are as follows:

6.00 g of 4,4'-dibromo-2,2'-diiodobiphenyl was dissolved in 100 mL of a mixed solvent of dichloromethane and ethyl acetate in the volume ratio of 1:1, then cooled to −75° C., and 30.00 mL of phenyl lithium solution (phenyl lithium/n-hexane in 1.0 M,) was added dropwise. Following 10 hours of reaction, 14.56 g of bis-eicosyl dichlorosilane was added, and the reaction was continued for another 34 hours, after the reaction was completed, a water was added and the mixture was extracted with diethyl ether, dried over anhydrous magnesium sulfate, rotary evaporated, and column chromatographed to give the product, MALDI-TOF-MS (m/z): 901.2 ($M^+$);

2) Preparation of 2,7-bis(4,4,5,5-tetramethyl-1,3,2-dioxaborolan)-9,9-bis-eicosyl silafluorene, and the structural formula and preparation process are as follows:

At −78° C., under a nitrogen atmosphere, 20.00 mL (1.00 M) of n-butyl lithium solution was added to a reaction flask containing 4.50 g of 2,7-dibromo-9,9-bis-eicosyl silafluorene and 100 mL of diethyl ether and stirred for 12 hours, then 4.17 mL of 2-isopropoxy-4,4,5,5-tetramethyl-1,3,2-dioxaborolane was added dropwise slowly, and stirred for another 48 hours. After the reaction was completed, the fluid mixture was poured into water then the solution was extracted with diethyl ether, dried over anhydrous magnesium sulfate, rotary evaporated, and column chromatographed to give a solid product, MALDI-TOF-MS (m/z): 995.3 ($M^+$);

3) Preparation of 3,7-bis(4-eicosyl thiophen-2-yl)-9,9-bis-eicosyl silafluorene, the structural formula and preparation process thereof are as follows:

Under the protection of nitrogen, to a reaction flask containing 3.00 g of 2,7-bis(4,4,5,5-tetramethyl-1,3,2-dioxaborolan)-9,9-bis-eicosyl silafluorene, 2.92 g of 2-bromo-4-eicosyl thiophene and 0.25 g of $Pd_2(dba)_3$/P(o-Tol)$_3$, 30 mL of aqueous tetraethyl ammonium hydroxide solution (1 M) and ethylene glycol dimethyl ether (50 mL) were added, then purged with nitrogen for 1 hour, and heated at 90° C. for 28 hours. After the reaction was completed, the mixture was filtered and dried in vacuo, column chromatographed to give a solid product, MALDI-TOF-MS (m/z): 1468.7 ($M^+$);

4) Preparation of 3,7-bis(5-bromo-4-eicosyl thiophen-2-yl)-9,9-bis-eicosyl silafluorene, and the structural formula and preparation process are as follows:

At 30° C., 0.73 g of NBS was added in batch to a reaction flask containing 2.94 g of 5,5-bis-eicosyl-3,7-bis(4-eicosyl-thiophen-2-yl)-4H-bis(silafluorene) and 40 mL of DMF, stirred for 18 hours. After the reaction was completed, the fluid mixture was poured into ice-water for quenching, then the solution was extracted with chloroform, and dried over anhydrous magnesium sulfate, rotary evaporated, and column chromatographed to give the product, MALDI-TOF-MS (m/z): 1626.5 ($M^+$);

5) Preparation of the quinoid silafluorene organic semiconductor material of structural formula $I_4$, the preparation process is as follows:

In ice bath, 0.88 g of malononitrile was added to the suspension of 0.20 g of sodium hydride (sodium hydride in an oil solution in 60 wt %) in 40 mL of ethylene glycol dimethyl ether, then warmed to room temperature and stirred for 30 minutes, to the mixture 1.63 g of 5,5-bis-eicosyl-3,7-bis(5-bromo-4-eicosyl-thiophen-2-yl)-4H-bis(silafluorene) and 0.055 g of $PdCl_2(PPh_3)_2$ were added, heated at 100° C. for 25 hours, then cooled to 0° C., and a saturated $Br_2/H_2O$ solution was added, then a water was added, and the solution was vacuum filtered, washed with water, dried, and column chromatographed to give the product, MALDI-TOF-MS (m/z): 1594.7 ($M^+$);

Example 5

Preparation of the Quinoid Silafluorene Organic Semiconductor Material of Following Structural Formula $I_5$ (I$_5$)

1) Preparation of 2,7-bis(4,4,5,5-tetramethyl-1,3,2-dioxaborolan)-9,9-dihexyl silafluorene, the detailed preparation process is the same as step 2) of Example 2, and its structural formula is as follows:

2) preparation of 3,7-bis(2,2'-bithiophen-5-yl)-9,9-dihexyl silafluorene, the structural formula and preparation process thereof are as follows:

under the protection of nitrogen, to a reaction flask containing 3.01 g of 2,7-bis(4,4,5,5-tetramethyl-1,3,2-dioxaborolan)-9,9-dihexyl silafluorene, 2.50 g of 5-bromo-2,2'-bithiophene and 0.21 g of Pd(PPh$_3$)$_2$Cl$_2$, 30 mL aqueous NaHCO$_3$ solution (1 M), and ethylene glycol dimethyl ether (50 mL) were added. Following purged with nitrogen for 1 hour, the mixture was heated at 100° C. for 25 hours, after the reaction was completed, the mixture was filtered and dried in vacuo, then column chromatographed to give a solid product, MALDI-TOF-MS (m/z): 679.1 (M$^+$);

3) Preparation of 3,7-bis(5'-bromo-2,2'-bithiophen-5-yl)-9,9-dihexyl silafluorene, the structural formula and preparation process thereof are as follows:

At 10° C., 0.71 g of NBS was added in batch to a reaction flask containing 1.36 g of 5,5-dihexyl-3,7-bis(2,2'-bithiophen-5-yl)-4H-bis(silafluorene) and 20 mL of chloroform, stirred for 12 hours. After the reaction was completed, the fluid mixture was poured into ice-water for quenching, and the solution was extracted with chloroform, dried over anhydrous magnesium sulfate, rotary evaporated, and column chromatographed to give the product, MALDI-TOF-MS (m/z): 836.9 (M$^+$);

4) Preparation of the quinoid silafluorene organic semiconductor material of structural formula I$_5$, the preparation process is as follows:

in ice bath, 0.33 g of malononitrile was added to the suspension of 0.20 g of sodium methoxide in 40 mL of ethylene glycol dimethyl ether, then the mixture was warmed to room temperature and stirred for 30 minutes, then 0.84 g of 5,5-dihexyl-3,7-bis(5'-bromo-2,2'-bithiophen-5-yl)-4H-bis(silafluorene) and 0.043 g of PdCl$_2$(PPh$_3$)$_2$ were added, and the resulting mixture was heated at 110° C. for 33 hours, then cooled to 0° C., a saturated Br$_2$/H$_2$O solution was added, then a water was added, and the mixture was vacuum filtered, washed with water, dried, and column chromatographed to give the product, MALDI-TOF-MS (m/z): 805.2 (M$^+$).

Example 6

Preparation of the Quinoid Silafluorene Organic Semiconductor Material of Following Structural Formula I$_6$ 1) Preparation of 2,7-bis(4,4,5,5-tetramethyl-1,3,2-dioxaborolan)-9,9-bis-eicosyl silafluorene, the detailed preparation process is the same as step 2) of Example 2, and its structural formula is as follows:

2) 3,7-bis(4,4'-bis-eicosyl-2,2'-bithiophen-5-yl)-9,9-bis-eicosyl silafluorene, the structure formula and preparation process thereof are as follows:

To a reaction flask containing 9.95 g of 2,7-bis(4,4,5,5-tetramethyl-1,3,2-dioxaborolan)-9,9-bis-eicosyl silafluorene, 16.20 g of 5-bromo-4,4'-bis-eicosyl-2,2'-bithiophene and 0.55 g of Pd(PPh$_3$)$_4$, 60 mL of aqueous NaHCO$_3$ solution (1 M) and a mixed solvent (100 mL) of diethyl ether and dichloromethane in a volume ratio of 1:1 were added, then the mixture was heated at 85° C. for 32 hours. After the completion of the reaction, the resulting mixture was filtered and dried in vacuo, and column chromatographed to give a solid product, MALDI-TOF-MS (m/z): 2194.0 (M$^+$);

3) 3,7-bis(5'-bromo-4,4'-bis-eicosyl-2,2'-bithiophen-5-yl)-9,9-bis-eicosyl silafluorene, the structural formula and preparation process thereof are as follows:

At 25° C., 0.77 g of NBS was added in batch to a reaction flask containing 2.19 g of 5,5-bis-eicosyl-3,7-bis(4,4'-bis-eicosyl-2,2'-bithiophen-5-yl)-4H-bis(silafluorene) and 40 mL of mixed solvent of tetrahydrofuran and ethyl acetate in a volume ratio of 1:3, then the mixture was stirred for 18 hours. After the completion of the reaction, the fluid mixture was poured into ice water for quenching, then the solution was extracted with chloroform, dried over anhydrous magnesium sulfate, rotary evaporated, and column chromatographed to give the product, MALDI-TOF-MS (m/z): 2351.8 (M$^+$);

4) Preparation of the quinoid silafluorene organic semiconductor material of structural formula I$_6$, the preparation process thereof is as follows:

In ice bath, 0.49 g of malononitrile was added to the suspension of 0.10 g of sodium tert-butoxide (sodium tert-butoxide in an oil solution in 60 wt %) in 20 mL of ethylene glycol dimethyl ether, then the mixture was warmed to room temperature and stirred for 40 minutes, and 1.18 g of 5,5-bis-eicosyl-3,7-bis(5'-bromo-4,4'-bis-eicosyl-2,2'-bithiophen-5-yl)-4H-bis(silafluorene) and 0.033 g of PdCl$_2$(PPh$_3$)$_2$ were added, and the mixture was heated at 95° C. for 42 hours, then cooled to 0° C., and a saturated Br$_2$/H$_2$O solution was added, a water was added, then the resulting mixture was vacuum filtered, washed with water, dried, and column chromatographed to give the product, MALDI-TOF-MS (m/z): 2320.1 (M$^+$).

Application Example 7

Figure 2:
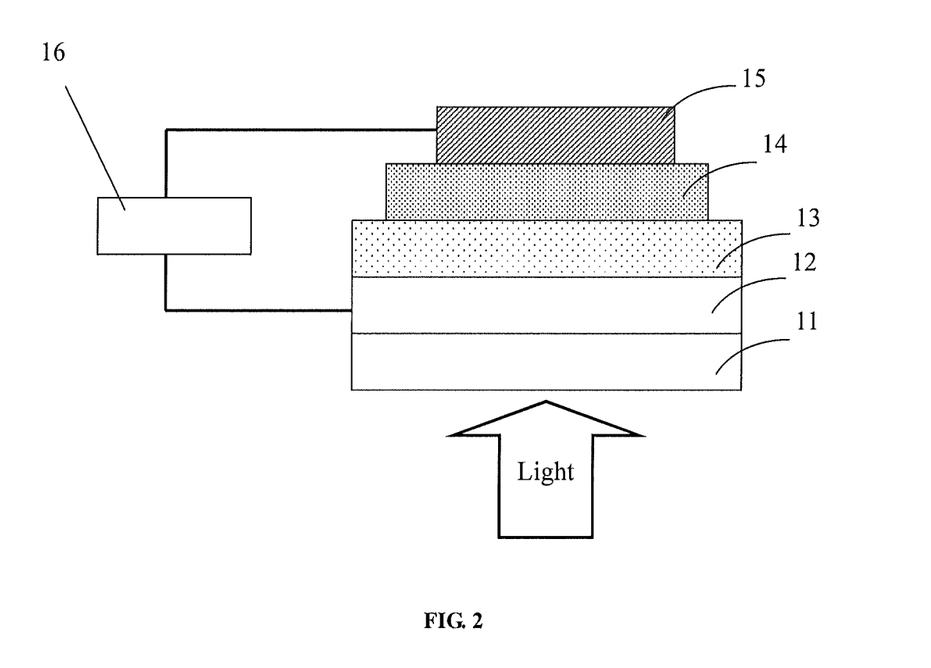
FIG. 2 is a structural schematic view of a organic solar cell device comprising the quinoid silafluorene organic semiconductor material prepared in Example 1 as an active layer.

Preparation of Solar Cell Device Containing the Quinoid Silafluorene Organic Semiconductor Material Made in Example 1 as an Active Layer Referring to FIG. 2, the solar cell device comprises a glass substrate 11, a transparent anode 12, a middle auxiliary layer 13, an active layer 14, a cathode 15 in a stacked structure, wherein the middle auxiliary layer 13 is made from poly(3,4-ethylenedioxythiophene): polystyrene-sulfonic acid composite (abbreviated as PEDOT:PSS), the active layer 14 includes an electron donor material and an electron acceptor material, and the electron donor material is made from the quinoid silafluorene organic semiconductor material made in Example 1, the electron acceptor material may be [6,6]phenyl-$C_{61}$-butyric acid methyl ester (abbreviated as PCBM). The transparent anode 12 may be made from Indium Tin Oxide (abbreviated as ITO), preferably from the Indium Tin Oxide with the sheet resistance of 10-20Ω/□. The cathode 15 may be an aluminum electrode or a double-metal-layer electrode, for example, Ca/Al, or Ba/Al and the like. The glass substrate 11 may be used as the bottom layer. In manufacturing, an ITO glass is selected, then it is ultrasonic washed, and treated with Oxygen-Plasma, then the middle auxiliary layer 13 is coated on the ITO glass, and the quinoid silafluorene organic semiconductor material made in Example 1 and the electron acceptor material are blended before coated on the middle auxiliary layer 13, thus formed the active layer 14 thereon, then the cathode 15 is deposited on the active layer 14 by vacuum evaporation to obtain the solar cell device. In a preferred embodiment, the thicknesses of the transparent anode 12, middle auxiliary layer 13, active layer 14, double-metal-layer Ca—Al layers are 170, 40, 150, 70 nm respectively.

Referring to FIG. 2, under illumination, the light passes through the glass substrate 11 and the ITO electrode 12, and the quinoid silafluorene organic semiconductor material made in Example 1 in the active layer 14 absorbs light energy and generates exactions, then these exactions migrate to the interface between the electron donor/acceptor materials, and the electron is transferred to the electron acceptor material, such as PCBM, so as to achieve the separation of the charge, and to produce free carriers, i.e. free electrons and holes. These free electrons are transferred along the electron acceptor material towards the metal cathode and collected by the cathode, meanwhile the free holes are transferred along the electron donor material towards the ITO anode and collected by the anode, to give photocurrent and photovoltage, and the photoelectric conversion is achieved. When there is an external load 16 connected to the device, the device will supply power to the external load. In this process, the quinoid silafluorene organic semiconductor material prepared in Example 1 may utilize the light energy more sufficiently due to its very wide spectral response range, and have higher photoelectric conversion efficiency, thus the power production capacity of the solar cell device is increased. Furthermore this organic material may reduce the weight of the solar cell device containing the same, and can be produced by spin coating technology, and may be prepared in large scale.

Application Example 8

Preparation of Organic Electroluminescent Apparatus Containing the Quinoid Silafluorene Organic Semiconductor Material Made in Example 1

Figure 3:
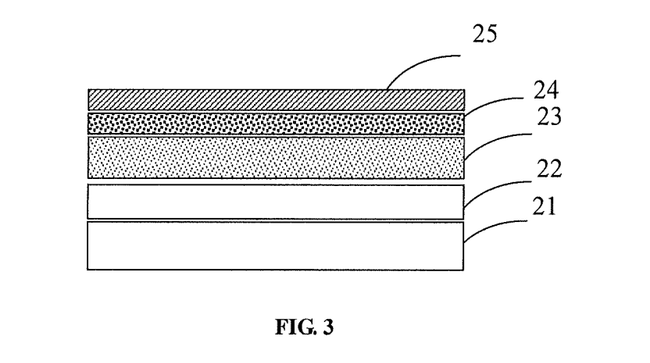
FIG. 3 is a structural schematic view of an organic electroluminescent device comprising the quinoid silafluorene organic semiconductor material prepared in Example 1 as a luminescent layer.

Referring to FIG. 3, an organic electroluminescent apparatus containing the quinoid silafluorene organic semiconductor material made in Example 1 is shown, the apparatus includes a glass substrate 21, a transparent anode 22, a luminescent layer 23, a buffer layer 24 and a cathode 25 in a stacked structure. The transparent anode 22 may be made from Indium Tin Oxide (abbreviated as ITO), preferably from the Indium Tin Oxide with the sheet resistance of 10-20Ω/□. The luminescent layer 23 includes the quinoid silafluorene organic semiconductor material prepared in the Example 1. The buffer layer 24 may be made from, but not limited to, LiF and the like. The cathode 25 may be Al and the like, but not limited thereto. Therefore, in a particular embodiment, the organic electroluminescence apparatus may be represented by the structure: ITO/the quinoid silafluorene organic semiconductor material made in Example 1/LiF/Al. Each of the layers may be made by the exiting method, and the quinoid silafluorene organic semiconductor material made in Example 1 may be formed on the ITO by spin coating. The LiF buffer layer may be vacuum evaporated on the luminescent layer, and the metal Al may be evaporated on the buffer layer and used as a cathode of the apparatus.

Application Example 9

Preparation of Organic Field Effect Transistor Containing the Quinoid Silafluorene Organic Semiconductor Material Made in Example 1

Figure 4:
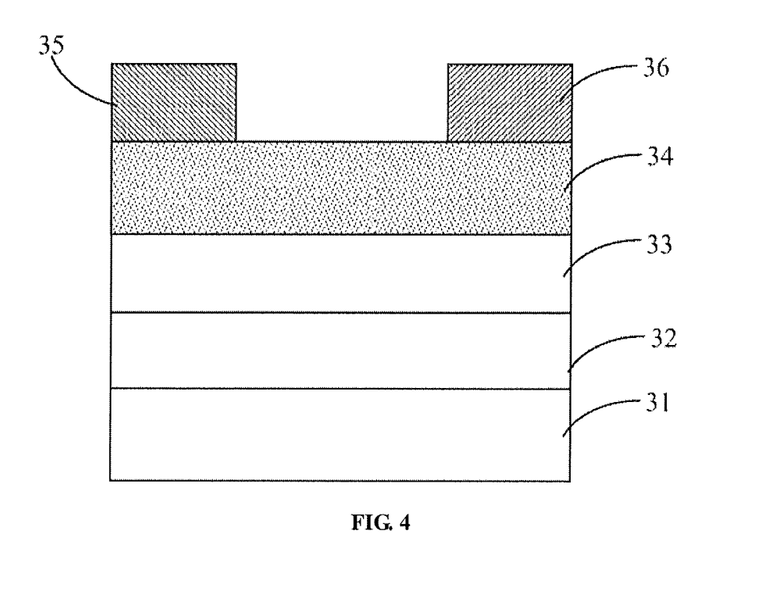
FIG. 4 is a structural schematic view of an organic field effect transistor device comprising the quinoid silafluorene organic semiconductor material prepared in Example 1 as an organic semiconductor layer.

Referring to FIG. 4, the organic field effect transistor contains a substrate 31, an insulating layer 32, a modifying layer 33, an organic semi-conductor layer 34 and a source electrode 35 and a drain electrode 36 disposed on the organic semi-conductor layer 34 in a stacked structure. Wherein the substrate 31 may be, but not limited to heavy doped silicon (Si), the insulating layer 32 may be, but not limited to, $SiO_2$ with the thickness of micro-nanometer (e.g., 450 nm). The organic semi-conductor layer 34 is made of the quinoid silafluorene organic semiconductor material prepared in Example 1. Both of the source electrode 35 and the drain electrode 36 may be made from aurum, but not limited thereto. The modifying layer 33 may be, but not limited to, octadecyl trichlorosilane (OTS). Each of the substrate 31, the insulating layer 32, the modifying layer 33 and the source electrode 35 and the drain electrode 36 may be made by the exiting method. The organic semi-conductor layer 34 may be made by spin coating the quinoid silafluorene organic semiconductor material prepared in the Example 1 on the insulating layer 32 modified by modifying layer 33 under a vacuum degree of nearly $10^{-4}$ Pa.

The embodiments above are merely the preferable embodiments of the present invention and not intended to limit the present invention. And all changes, equivalent substitution and improvements which come within the meaning and range of equivalency of the present invention are intended to be embraced therein.

What is claimed:

1. A quinoid silafluorene organic semiconductor material, the general formula (I) thereof is:

wherein, $R_1$, $R_2$, $R_5$ and $R_6$ are independently selected from the group consisting of —H and $C_1$-$C_{20}$ alkyl, $R_3$ and $R_4$ are independently $C_1$-$C_{20}$ alkyl, m and n are independently integers of 0-10.

2. The quinoid silafluorene organic semiconductor material of claim 1, wherein the $R_1$, $R_2$, $R_5$ and $R_6$ are independently selected from the group consisting of —H, —$C_6H_{13}$ and —$C_{20}H_{41}$ alkyl, $R_3$ and $R_4$ are independently selected from the group consisting of —$CH_3$, —$C_6H_{13}$ and —$C_{20}H_{41}$ alkyl.

3. A method for manufacturing a quinoid silafluorene organic semiconductor material, comprising:
compounds A, B, C and D with the following general formulae are provided separately:

A:

B:

C:

D:

wherein $R_1$, $R_2$, $R_5$ and $R_6$ are independently selected from the group consisting of —H and —$C_1$-$C_{20}$ alkyl, $R_3$ and $R_4$ are independently $C_1$-$C_{20}$ alkyl, m and n are independently integers of 0-10;
in an alkaline environment and with the presence of a catalyst and an organic solvent, a Suzuki coupling reaction of compounds A, B and C is carried out to give the compound E of the following formula:

(E)

with the presence of an organic solvent, a bromination reaction of compound E and N-bromo-succinimide is carried out to give a dibromo compound of compound E;
with the presence of a catalyst, a condensing agent and an organic solvent, a condensation reaction of the dibromo compound of compound E and malononitrile is carried out to give the quinoid silafluorene organic semiconductor material of general formula (I), wherein m and n are independently integers of 1-10;
alternatively, with the presence of a catalyst, a condensing agent and an organic solvent, a condensation reaction of compound D and malononitrile is carried out to give the quinoid silafluorene organic semiconductor material of general formula (I), wherein m=n=0, (I)

4. The method for manufacturing a quinoid silafluorene organic semiconductor material of claim 3, wherein the method for manufacturing compound A comprises:
with the presence of an organic solvent, the reaction of 4,4'-dibromo-2,2'-diiodo-biphenyl, alkyl lithium derivative and dialkyl dichlorosilane is carried out to give 2,7-dibromo-9,9-dialkylsilafluorene compound;
with the presence of an organic solvent, the condensation reaction of 2,7-dibromo-9,9-dialkyl silafluorene compound, alkyl lithium derivative, 2 isopropoxy-4,4,5,5-tetramethyl-1,3,2-dioxaborolane is carried out to give the compound A.

5. The method for manufacturing a quinoid silafluorene organic semiconductor material of claim 4, wherein
the molar ratio of the 4,4'-dibromo-2,2'-diiodo-biphenyl, alkyl lithium derivative, dialkyl dichlorosilane in the preparation process of the 2,7-dibromo-9,9-dialkylsilafluorene compound is 1.0:2.0-4.0:2.0-4.0;
the reaction temperature in the preparation process of the 2,7-dibromo-9,9-dialkylsilafluorene compound is −100~−25° C., the duration thereof is 24-48 hours;
the organic solvent in the preparation process of the 2,7-dibromo-9,9-dialkylsilafluorene compound is one or more selected from the group consisting of tetrahydrofuran, diethyl ether, dichloromethane, chloroform and ethyl acetate.

6. The method for manufacturing a quinoid silafluorene organic semiconductor material of claim 4, wherein
the molar ratio of 2,7-dibromo-9,9-dialkyl silafluorene compound, alkyl lithium derivative, 2-isopropoxy-4,4,5,5-tetramethyl-1,3,2-dioxaborolane in the condensation reaction is 1.0:2.0-4.0:2.0-4.0;
the reaction temperature of the condensation reaction is −100~−25° C., the duration thereof is 24-48 hours;
the organic solvent in the condensation reaction is one or more selected from the group consisting of tetrahydrofuran, diethyl ether, dichloromethane, chloroform and ethyl acetate.

7. The method for manufacturing a quinoid silafluorene organic semiconductor material of claim 3, wherein
the molar ratio of the compounds A, B and C in the Suzuki coupling reaction is 1.0:1.0-1.5:1.0-1.5;
the temperature of the Suzuki coupling reaction is 75-120° C., the duration thereof is 12-72 hours;
the alkali in the alkaline environment is one or more selected from the group consisting of NaOH, $Na_2CO_3$, $NaHCO_3$ and tetraethyl ammonium hydroxide;
the catalyst is one or more selected from the group consisting of $Pd(PPh_3)_4$, $Pd_2(dba)_3$/P(o-Tol)$_3$, $Pd(PPh_3)_2Cl_2$, and the amount thereof is 0.05%-20% molar percent of that of the compound A; and the organic solvent is one or more selected from the group consisting of ethylene glycol dimethyl ether, tetrahydrofuran, diethyl ether, dichloromethane, chloroform and ethyl acetate.

8. The method for manufacturing a quinoid silafluorene organic semiconductor material of claim 3, wherein
the molar ratio of compound E and N-bromo-succinimide in the bromination reaction is 1.0:2.0-2.5;
the temperature of the bromination reaction is −5~30° C., the duration thereof is 12-48 hours; and
the organic solvent is one or more selected from the group consisting of N,N-dimethyl formamide, tetrahydrofuran, diethyl ether, dichloromethane, chloroform, ethyl acetate and acetic acid.

9. The method for manufacturing a quinoid silafluorene organic semiconductor material of claim 3, wherein
the molar ratio of the dibromo compound of compound E and malononitrile in the condensation reaction is 1.0:2.0-10;
the temperature of the condensation reaction is 75-120° C., the duration thereof is 12-72 hours;
the organic solvent is one or more selected from the group consisting of ethylene glycol dimethyl ether, tetrahydrofuran, diethyl ether, dichloromethane, chloroform and ethyl acetate;
the catalyst is organic Pd, the amount thereof is 0.05%-20% molar percentage of that of the dibromo compound of compound E; and
the condensing agent is one or more selected from the group consisting of NaH and sodium alkoxide.

* * * * *